United States Patent
Yu et al.

(10) Patent No.: US 12,297,415 B2
(45) Date of Patent: May 13, 2025

(54) FULLY ENCLOSED CELL CULTURE SYSTEM

(71) Applicant: HUADAO (SHANGHAI) BIOPHARMA CO., LTD., Shanghai (CN)

(72) Inventors: Xuejun Yu, Shanghai (CN); Peng Xu, Shanghai (CN); Yongjun Fang, Shanghai (CN); Dongge Feng, Shanghai (CN)

(73) Assignee: Huadao (Shanghai) Biopharma Co., Ltd., Shanghai (CN)

( * ) Notice: Subject to any disclaimer, the term of this patent is extended or adjusted under 35 U.S.C. 154(b) by 204 days.

(21) Appl. No.: 17/216,699

(22) Filed: Mar. 30, 2021

(65) Prior Publication Data

US 2022/0348851 A1 Nov. 3, 2022

Related U.S. Application Data

(63) Continuation-in-part of application No. PCT/CN2019/098474, filed on Jul. 31, 2019.

(30) Foreign Application Priority Data

Mar. 12, 2019 (CN) .......................... 201910184785.5
Mar. 12, 2019 (CN) .......................... 201920312979.4

(51) Int. Cl.
*C12M 1/00* (2006.01)
*C12M 1/02* (2006.01)
(Continued)

(52) U.S. Cl.
CPC ................ *C12M 3/00* (2013.01); *C12M 1/02* (2013.01); *C12M 1/04* (2013.01); *C12M 1/38* (2013.01); *C12M 41/14* (2013.01)

(58) Field of Classification Search
CPC ....................................................... C12M 41/14
See application file for complete search history.

(56) References Cited

U.S. PATENT DOCUMENTS

| | | | | |
|---|---|---|---|---|
| 4,336,329 A | * | 6/1982 | Hesse | C12N 1/00 422/298 |
| 2019/0048305 A1 | * | 2/2019 | De | C12M 29/10 |
| 2022/0002652 A1 | * | 1/2022 | Patrick | C12M 21/00 |

FOREIGN PATENT DOCUMENTS

| CN | 102212473 A | 10/2011 |
|---|---|---|
| CN | 105385597 A | 3/2016 |

(Continued)

*Primary Examiner* — Jonathan M Hurst
(74) *Attorney, Agent, or Firm* — IPRTOP LLC (57) ABSTRACT

The present disclosure provides a fully enclosed cell culture system, including at least an incubator, a bioreactor, a gas flow assembly, a liquid flow assembly, a temperature adjustment assembly, and a central controller. The system realizes a thermostatic incubation environment. Cells are incubated by perfusion, and a fully enclosed integrated process from cell activation, infection and amplification to finished product harvesting is achieved. By axially stirring the cells and an incubation liquid in a tank body, a radial shear force is reduced, which effectively protects the cells and improves the cell yield. In the system of the present disclosure, gases are separately introduced, ensuring that the content of each gas component is stable in the incubation process. The cell incubation is not directly affected by changes of outside gases in the cell incubation process, which improves culture efficiency.

7 Claims, 7 Drawing Sheets

(51) Int. Cl.
*C12M 1/04* (2006.01)
*C12M 1/38* (2006.01)
*C12M 3/00* (2006.01)

(56) References Cited

FOREIGN PATENT DOCUMENTS

| CN | 205506791 U | 8/2016 |
| CN | 105925481 A | 9/2016 |
| CN | 109825436 A | 5/2019 |

* cited by examiner

FULLY ENCLOSED CELL CULTURE SYSTEM

CROSS REFERENCES TO RELATED APPLICATIONS

The present application is a continuation-in-part application of a PCT/CN2019/098474 filed on Jul. 31, 2019; the PCT/CN2019/098474 claims priorities of the CN 201910184785.5 filed on Mar. 12, 2019 and the CN 201920312979.4 filed on Mar. 12, 2019, which applications are incorporated herein by reference.

FIELD OF TECHNOLOGY

The present disclosure relates to the field of cell culture technology, and in particular, to a fully enclosed cell culture system.

BACKGROUND

In recent years, Chimeric Antigen Receptor T-Cell (CAR-T cell) immunotherapy has been considered one of the most promising treatments for cancers. CAR-T cell immunotherapy has many advantages over other treatments. For example, CAR-T cells may bind to multiple targeted sites, which improve the accuracy of tumor treatment, and its treatment process is not restricted by the major histocompatibility complex (MHC); CAR-T cells are able to kill a wider range of tumors and they have longer lasting effects; CAR-T cell immunotherapy has good technical properties and replicability. FDA approved two CD19 CAR-T cell drugs (Kymriah and Yescarta, respectively) which have achieved good results in the treatment of hematological malignancies in 2018. However, CAR-T cell immunotherapy still has many limitations, such as the preparation of CAR-T cells. In the process of CAR-T treatment, the number of the genetically modified T cells need to be cultured in vitro to reach hundreds of millions or even billions that required by treatments, then infuse CAR-T cells into the patient to kill cancer cells. However, CAR-T cells take a long time to prepare in vitro due to limited by current technical means, thereby prolonging the clinical treatment period.

Cell culture refers to a method that simulates the internal environment (sterile, suitable temperature, pH, and certain nutritional conditions, etc.) in vitro to enable cells to survive, grow, proliferating and maintain main structures and functions. Cell culture technology is an important and commonly used technology in cell biology research. By using cell culture technology, a large number of cells may be obtained. Cell culture technology may also be utilized to research cell signal transduction, cell anabolism, and cell growth and proliferation.

Currently, most cell cultures are prepared manually by operators. Therefore, when a large number of cultured cells are needed for industrialization, considerable costs of labor and time are required. At the same time, as the burden on the operators increases, the risk of errors also increases. Moreover, the operators cannot accurately control the simulated environment, which is not conducive to cell growth.

SUMMARY

The present disclosure provides a fully enclosed cell culture system. The fully enclosed cell culture system includes an incubator, a bioreactor, a gas flow assembly, a liquid flow assembly, a temperature adjustment assembly, and a central controller.

The bioreactor is configured to perform cell culture, and is disposed in the incubator; the bioreactor is provided with a stirrer, and the stirrer is disposed in the bioreactor.

The gas flow assembly is connected with the incubator, to adjust concentrations of oxygen and carbon dioxide in the incubator.

The liquid flow assembly is connected with the bioreactor, to adjust a liquid flow in the bioreactor, filter the metabolite, and harvest cells.

The temperature adjustment assembly is configured to adjust the temperature in the incubator.

The central controller is connected to and controls the gas flow assembly, the liquid flow assembly, and the temperature adjustment assembly.

The present disclosure provides a use of the aforementioned fully enclosed cell culture system for cultivating cells in a fully enclosed system.

The present disclosure also provides a method for obtaining a fully enclosed cell culture using the aforementioned fully enclosed cell culture system. The method includes:

1) perfusion: presetting a volume, and injecting culture medium into a bioreactor, the volume of the injected culture medium equals the preset volume (hereinafter, liquid feeding volume);
2) establishing a culture environment: presetting concentration values of oxygen and carbon dioxide, injecting oxygen and carbon dioxide into the incubator, monitoring gas concentration values of oxygen and carbon dioxide in the incubator in real time, and comparing the gas concentration values with the preset concentration values respectively; when either the oxygen or carbon dioxide's concentration values in the incubator reaches a threshold, injecting the gas in the incubator into the bioreactor; setting a temperature for the incubator and preheating the incubator;
3) continuous culturing: injecting cells, injecting factors, starting a stirrer, injecting the culture medium into the bioreactor, filtering metabolites, and discharging waste liquid;
4) replacing and concentrating: after the cell culture is completed, replacing the culture medium with saline solution; performing concentration after the replacement is completed; continuously discharging the waste liquid to reduce the amount of liquid in the bioreactor;
5) harvesting finished products: stopping the stirrer and harvesting finished cells in the bioreactor.

One or more aspects of the fully enclosed cell culture system have the following advantages:

The system of the present disclosure realizes a thermostatic incubation environment. Cells are incubated by perfusion, and a fully enclosed integrated process including cell activation, infection, amplification, and harvesting finished product is achieved. The system of the present disclosure adopts a perfusion method instead of a filling method. The waste liquid may be discharged during the incubation process to prevent the accumulation of harmful metabolites, which is beneficial for achieving a high cell culture density; further, subsequent processing steps may be reduced, and the finished cells may be harvested without centrifugation and other operations. In sum, the operations may be simplified, the culture efficiency is improved, the industrialization is facilitated, and a fully enclosed integrated process including cell activation, infection, amplification, and harvesting finished product is achieved. By axially stirring the cells and incubation liquid in a tank, radial shear forces are reduced, which protects the cells and improves the cell yield. In the system of the present disclosure, gases are separately introduced, ensuring that the content of each gas component is stable in the incubation process, the cell incubation is not directly affected by changes of outside gases in the cell incubation process, and the content of each gas component is unchanged. In the incubation process, the incubation temperature, liquid volume and gas concentration are controlled to keep the culture environment stable, while reducing manual operations, reducing the costs, and the risk of operating errors in the incubation process, and improving culture efficiency.

LIST OF REFERENCE NUMERALS

1 Incubator
2 Bioreactor
2.1 Liquid inlet
2.2 First circulation port
2.3 Second circulation port
2.4 Harvest port
2.5 Stirrer
2.51 Center shaft
2.52 Blade
2.53 Enclosed accommodating chamber
2.6 Bioreactor lid
2.61 Lid body
2.62 Gas exhaust part
2.63 Gas intake part
2.7 Inner recess
3 Gas flow assembly
3.1 Air passage
3.1.1 Air filter
3.1.2 Air pipeline
3.1.3 Vent
3.2 Carbon dioxide passage
3.2.1 Carbon dioxide storage device
3.2.2 Carbon dioxide pressure relief valve
3.2.3 Carbon dioxide passage switch
3.2.4 Carbon dioxide pipeline
3.2.5 Carbon dioxide passage incubator inlet
3.3 Oxygen passage
3.3.1 Oxygen storage device
3.3.2 Oxygen pressure relief valve
3.3.3 Oxygen passage switch
3.3.4 Oxygen pipeline
3.3.5 Oxygen passage incubator inlet
3.4 Mixed gas suction passage
3.4.1 Mixed gas suction pump
3.4.2 Mixed gas suction pipeline
3.4.3 Mixed gas passage incubator outlet
3.5 Exhaust gas discharge passage
3.6 Gas concentration sensor segment
3.6.1 Oxygen gas concentration sensor
3.6.2 Carbon dioxide gas concentration sensor
3.7 Gas discharge passage
3.8 Fan
4 Liquid flow assembly
4.1 Liquid inlet passage
4.1.1 Liquid storage bag
4.1.2 Liquid inlet pipeline
4.1.3 Liquid inlet pump
4.1.5 Liquid level gauge
4.2 Circulation passage
4.2.1 Circulation pipeline
4.2.2 Circulation pump
4.2.3 Filter
4.3 Waste liquid passage
4.3.1 Waste liquid pump
4.3.2 Waste liquid barrel
4.3.3 Waste liquid pipeline
4.4 Harvest passage
4.4.1 Harvest pipeline
4.4.2 Harvest pump
4.4.3 Harvest bag
4.5 Weighing sensor
5 Temperature adjustment assembly
5.1 Heating device
5.2 Temperature sensor
6 Central controller
7 Sterilizing lamp
8 Stirring driver

DETAILED DESCRIPTION

One or more specific embodiments of the present disclosure will be described below. These described embodiments are only examples of the presently disclosed techniques, and are not intended to limit aspects of the presently disclosed invention. Additionally, in an effort to provide a concise description of these embodiments, all features of an actual implementation may not be described in the specification. It should be appreciated that in the development of any such actual implementation, numerous implementation-specific decisions must be made to achieve the developers' specific goals, which may vary from one implementation to another. Referring to FIGS. 1-7. It should be understood that the structures, proportions, sizes, and the like, which are illustrated in the drawings of the present specification, are only used to clarify the contents disclosed in the specification for understanding and reading by those skilled, and are not intended to limit the implementation of the present disclosure, thus are not technically meaningful. Any modification of the structure, change of the scale, or adjustment of the size should still fall within the scope of the technical contents disclosed by the present disclosure without affecting the effects and achievable objectives of the present disclosure. In the meantime, the terms "upper", "lower", "left", "right", "intermediate" and "one" as used in this specification are also for convenience of description, and are not intended to limit the scope of the present disclosure, and the change or adjustment of the relative relationship is considered to be within the scope of the present disclosure without substantial changes in technology.

It should be noted that the central controller of the present disclosure may be located at any position on the outer wall of the incubator, or on a console outside the incubator, as long as the central controller is connected to other components in the fully enclosed cell culture system. Therefore, the position of the central controller is not shown in FIGS. 2-4.

As shown in FIGS. 1-4, the fully enclosed cell culture system of the present disclosure includes at least the following: an incubator 1; a bioreactor 2; a gas flow assembly 3; a liquid flow assembly 4; a temperature adjustment assembly 5; and a central controller 6.

Figure 1:
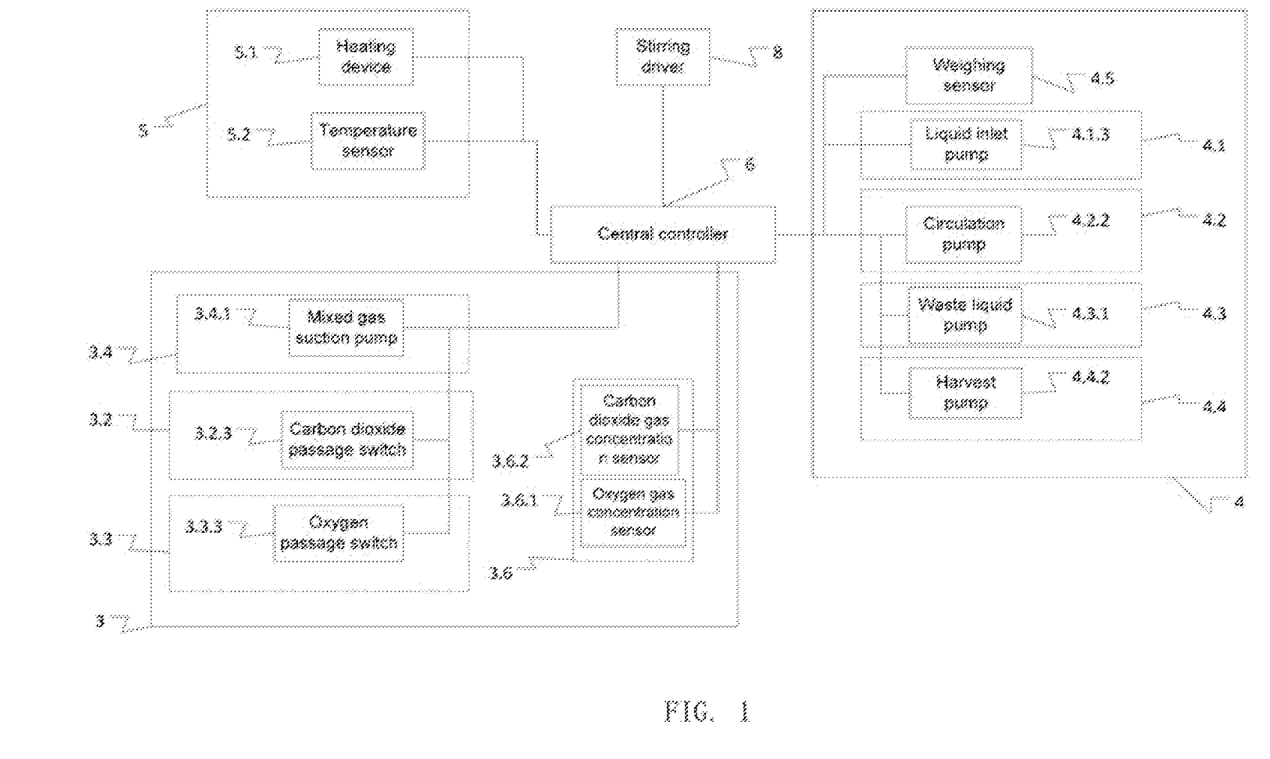
FIG. 1 shows a block diagram illustrating a fully enclosed cell culture system according to some embodiments.
Figure 2:
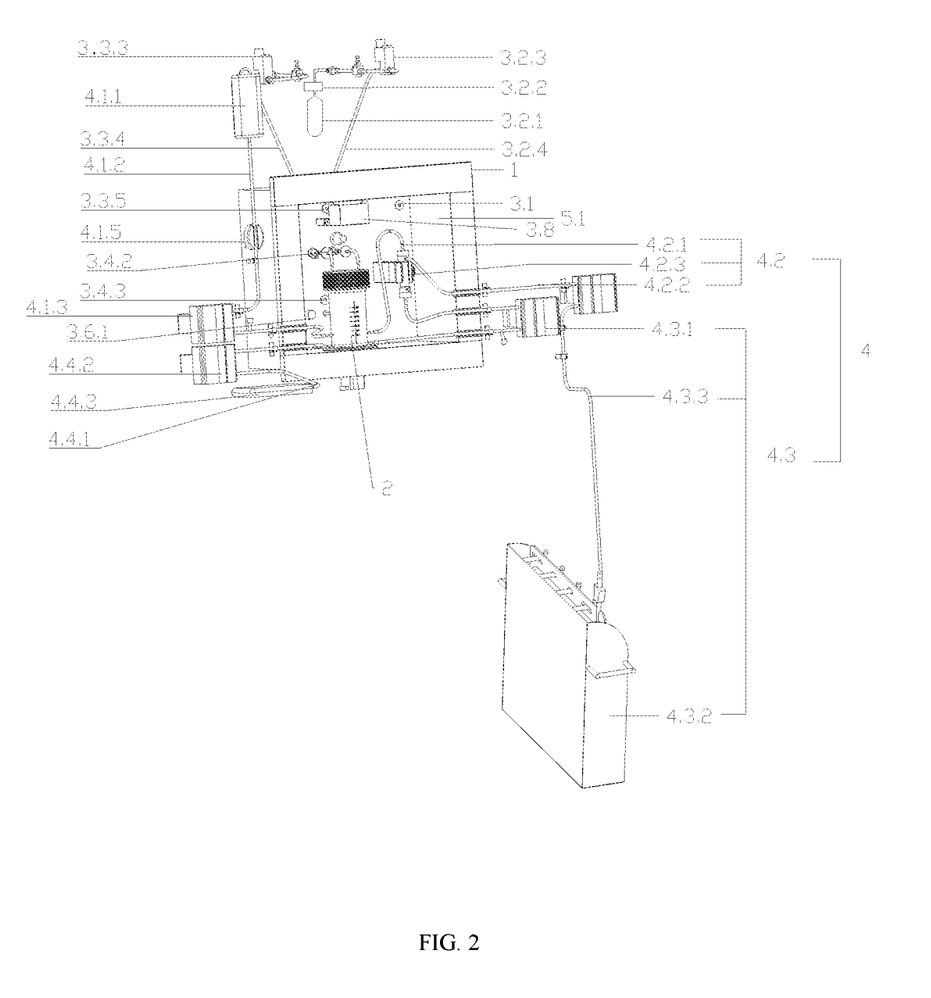
FIG. 2 shows a front view of a fully enclosed cell culture system according to some embodiments
Figure 3:
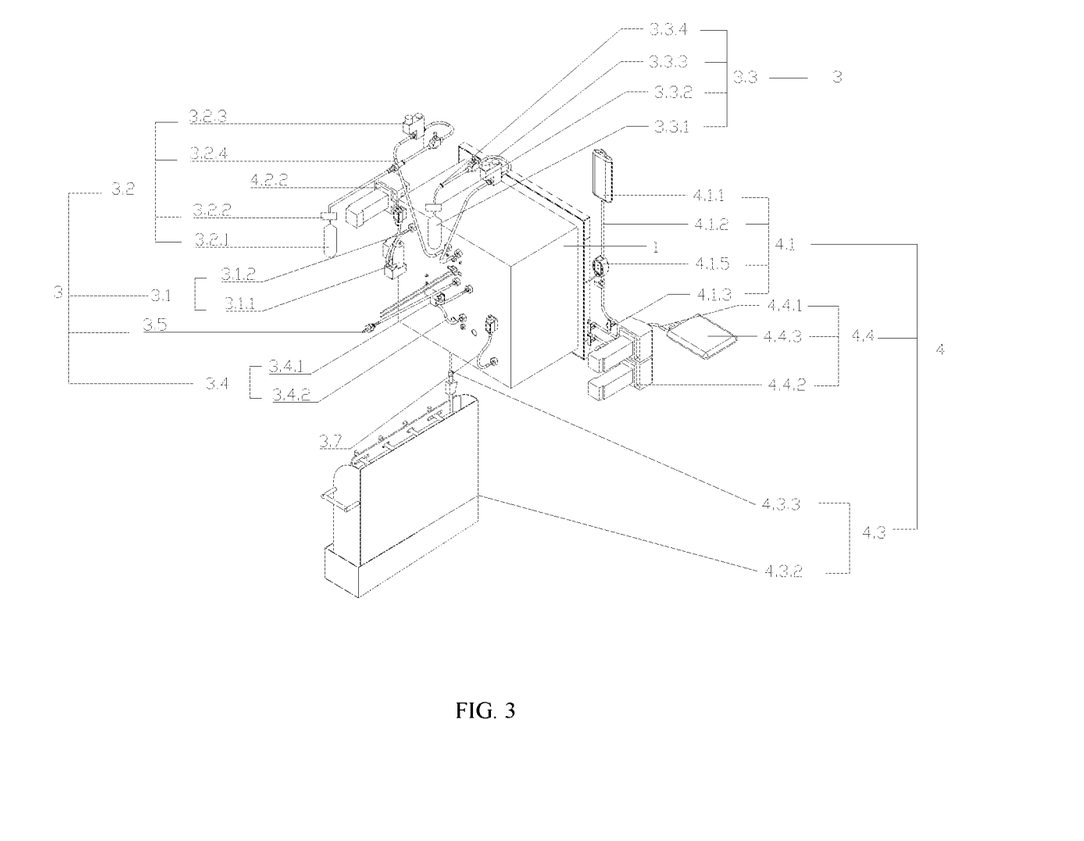
FIG. 3 shows a rear perspective view of a fully enclosed cell culture system according to some embodiments.
Figure 4:
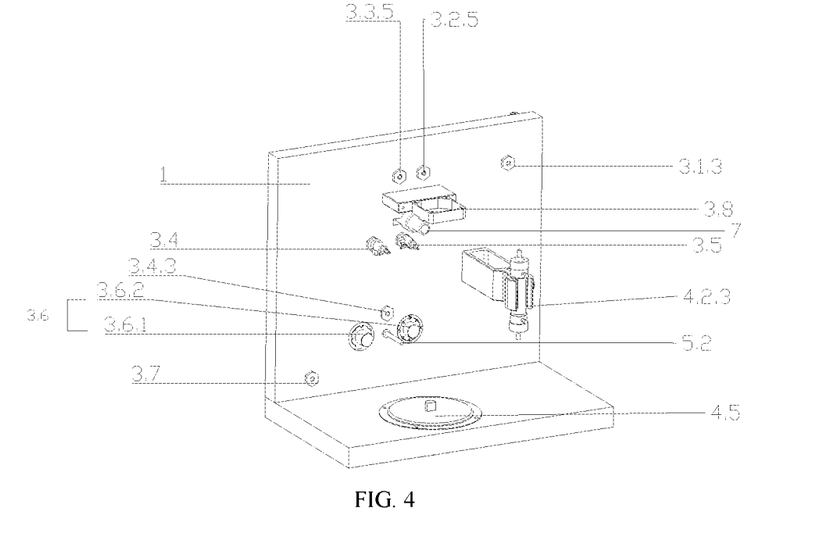
FIG. 4 shows the distribution of components in an incubator of a fully enclosed cell culture system according to some embodiments.

The incubator is configured to provide a stable culture environment, including a stable gas environment and temperature environment.

The bioreactor 2 is configured to perform cell culture, and is disposed in the incubator; the bioreactor 2 is provided with a stirrer, and the stirrer is disposed in the bioreactor 2.

The gas flow assembly 3 is connected with the incubator 1, to adjust concentrations of oxygen and carbon dioxide in the incubator 1.

The liquid flow assembly 4 is connected with the bioreactor 2. The liquid flow assembly 4 adjusts the liquid flow in the bioreactor 2, filters the metabolite produced by cell culture, and harvets finished cells.

The temperature adjustment assembly 5 is configured to adjust temperature in the incubator 1.

The central controller 6 is connected to and controls the gas flow assembly, the liquid flow assembly, and the temperature adjustment assembly.

The culture system of the present disclosure adopts a perfusion method instead of a filling method. Therefore, the waste liquid may be discharged during the incubation process to prevent accumulation of harmful metabolites, which is beneficial for achieving a high cell culture density; further, subsequent processing steps may be reduced, and the finished cells may be harvested without centrifugation and other operations; the operations may be simplified to facilitate cell harvest, the culture efficiency is improved, and the industrialization is facilitated.

Further, the gas flow assembly 3 includes:
- an air passage 3.1, a carbon dioxide passage 3.2, and an oxygen passage 3.3, which are separated from each other and respectively connected with the incubator 1 and deliver gas into the incubator 1 to form a gas mixture;
- a mixed gas suction passage 3.4, connected with the incubator 1 and the bioreactor 2 and configured to deliver the gas mixture in the incubator 1 into the bioreactor 2;
- an exhaust gas discharge passage 3.5, connected with the bioreactor 2 and configured to discharge exhaust gas generated during a cell culturing process;
- a gas concentration sensor segment 3.6, including an oxygen gas concentration sensor 3.6.1 and a carbon dioxide gas concentration sensor 3.6.2, the oxygen gas concentration sensor 3.6.1 and the carbon dioxide gas concentration sensor 3.6.2 are respectively configured to measure the real-time oxygen gas concentration value and the real-time carbon dioxide gas concentration value in the incubator 1, the gas concentration sensor segment 3.6 communicates with the central controller 6.

Further, the air passage 3.1 includes an air pipeline 3.1.2; the air pipeline 3.1.2 is in communication with the incubator 1. In an embodiment, the air passage 3.1 further includes an air filter 3.1.1, which filters air before entering the incubator 1.

The carbon dioxide passage 3.2 includes a carbon dioxide storage device 3.2.1, a carbon dioxide pressure relief valve 3.2.2, a carbon dioxide passage switch 3.2.3, and a carbon dioxide pipeline 3.2.4. The carbon dioxide storage device 3.2.1 is connected with the carbon dioxide pipeline 3.2.4. The carbon dioxide pipeline 3.2.4 is driven by the carbon dioxide pressure relief valve 3.2.2. The carbon dioxide pipeline 3.2.4 is in communication with the incubator 1. The carbon dioxide passage switch 3.2.3 is provided on the carbon dioxide passage 3.2, and the carbon dioxide passage switch 3.2.3 is controlled by the central controller 6.

In an embodiment, the carbon dioxide passage switch 3.2.3 is one or more of a carbon dioxide storage device switch, a carbon dioxide pipeline switch, and a carbon dioxide pressure relief valve switch. The carbon dioxide passage switch 3.2.3 may be a solenoid valve.

The oxygen passage 3.3 includes an oxygen storage device 3.3.1, an oxygen pressure relief valve 3.3.2, an oxygen passage switch 3.3.3, and an oxygen pipeline 3.3.4; the oxygen storage device 3.3.1 is connected with the oxygen pipeline 3.3.4, the oxygen pipeline 3.3.4 is driven by the oxygen pressure relief valve 3.3.2, and the oxygen pipeline 3.3.4 is in communication with the incubator 1; the oxygen passage switch 3.3.3 is provided on the oxygen passage 3.3, and the oxygen passage switch 3.3.3 is controlled by the central controller 6.

In an embodiment, the oxygen passage switch 3.3.3 is one or more of an oxygen storage device switch, an oxygen pipeline switch, and an oxygen pressure relief valve switch. The oxygen passage switch may be a solenoid valve.

The mixed gas suction passage 3.4 includes a mixed gas suction pump 3.4.1 and a mixed gas suction pipeline 3.4.2; the mixed gas suction pipeline 3.4.2 is driven by the mixed gas suction pump 3.4.1, and the mixed gas suction pipeline 3.4.2 is configured to inject the gas mixture from the incubator 1 into the bioreactor 2; the mixed gas suction pump 3.4.1 is controlled by the central controller 6.

In an embodiment, the mixed gas suction pipeline 3.4.2 is provided with a gas filter. The gas filter is configured to filter gas entering the bioreactor 2.

Further, the exhaust gas discharge passage 3.5 includes an exhaust gas discharge pipeline. The exhaust gas discharge pipeline is provided with a one-way valve to prevent outside air from entering the tank through the exhaust gas discharge pipeline.

The exhaust gas discharge passage 3.5 directly discharges the exhaust gas to the outside of the system.

Further, the incubator includes a gas discharge passage 3.7, which discharges the gas in the incubator 1 and stabilizes the air pressure in the incubator 1.

Further, the gas discharge passage 3.7 includes a gas discharge pipeline, which discharges the gas in the incubator 1 and stabilizes the air pressure in the incubator 1.

In an embodiment, the gas discharge passage 3.7 and the air passage 3.1 are the same passage.

In an embodiment, the carbon dioxide passage 3.2 includes a carbon dioxide passage incubator inlet 3.2.5 on the incubator 1; the oxygen passage 3.3 includes an oxygen passage incubator inlet 3.3.5 on the incubator 1. The carbon dioxide passage incubator inlet 3.2.5 and the oxygen passage incubator inlet 3.3.5 are both disposed in the upper part of the incubator 1. Cold air tends to sink to the bottom, while hot air rises. Therefore, after being injected into the upper part of the incubator 1, the gas may mix more quickly to obtain a homogeneous gas concentration throughout the incubator.

In an embodiment, the mixed gas suction passage 3.4 is provided with a mixed gas passage incubator outlet 3.4.3 on the incubator 1. The mixed gas passage incubator outlet 3.4.3, the oxygen gas concentration sensor 3.6.1, and the carbon dioxide gas concentration sensor 3.6.2 are disposed in the lower part of the incubator 1.

The air passage 3.1 and/or the gas discharge passage 3.7 are provided with a vent 3.1.3 on the incubator 1. The vent 3.1.3 is away from the carbon dioxide passage incubator inlet 3.2.5, the oxygen passage incubator inlet 3.3.5, the mixed gas passage incubator outlet 3.4.3, the oxygen gas concentration sensor 3.6.1, and the carbon dioxide gas concentration sensor 3.6.2, to prevent the gas from escaping too quickly.

In an embodiment, the incubator 1 is provided with a fan 3.8 for agitating gas flow, speeding up the mixing, making the gas in the incubator 1 more evenly mixed and accelerating heat exchange inside the incubator 1.

In an embodiment, the fan 3.8 is disposed in the upper part of the incubator 1.

Further, the central controller 6 includes a gas concentration comparison unit and a gas concentration switch control unit.

The gas concentration comparison unit is configured to compare a real-time oxygen gas concentration value $C_{tO2}$, measured by the gas concentration sensor segment 3.6 and a preset oxygen gas concentration value $C_{0O2}$. The gas concentration comparison unit is also configured to compare a real-time carbon dioxide gas concentration value $C_{tCO2}$, measured by the gas concentration sensor segment 3.6 and a preset carbon dioxide concentration value $C_{0CO2}$. $C_{O2}$ is the difference between $C_{0O2}$ and $C_{tO2}$, and $C_{CO2}$ is the difference between $C_{0CO2}$ and $C_{tCO2}$ as given by formulas (I) and (II):

$$C_{O2} = C_{0O2} - C_{tO2} \quad (I)$$

$$C_{CO2} = C_{0CO2} - C_{tCO2} \quad (II)$$

The gas concentration switch control unit is configured to control the opening and closing of the oxygen passage 3.3, the carbon dioxide passage 3.2, and the mixed gas suction passage 3.4.

More specifically, the opening and closing of the oxygen passage is determined according to the value of $C_{O2}$; the opening and closing of the carbon dioxide passage is determined according to the value of $C_{CO2}$; when both $C_{O2}$ and $C_{CO2}$ fall within preset ranges, the mixed gas suction passage 3.4 is opened, and the gas in the incubator 1 is sucked into the bioreactor 2; when either $C_{O2}$ or $C_{CO2}$ does not fall within its corresponding preset range, the mixed gas suction passage 3.4 is closed.

The oxygen gas concentration value $C_{0O2}$, the carbon dioxide concentration value $C_{0CO2}$ and the preset range mays be set according to the cells to be cultured. In an embodiment, the preset ranges of $C_{O2}$ and $C_{CO2}$ may be a range within −0.1% to 0.1%.

In an embodiment, when both $C_{O2}$ and $C_{CO2}$ fall within the preset range, the mixed gas suction passage 3.4 is opened by a timed operation, and the gas in the incubator 1 is sucked into the bioreactor 2. The timing of the timed operation is determined by the gas volume in the bioreactor 2 and the flow rate of the mixed gas suction pump. This means, when both $C_{O2}$ and $C_{CO2}$ fall within the set range, the mixed gas suction passage 3.4 is not opened immediately; instead, the opening and closing of the mixed gas suction passage 3.4 are controlled by the system and happen continuously after a fixed time set by the system.

Further, the opening and closing of the oxygen passage 3.3 are controlled by controlling the opening and closing of the oxygen passage switch 3.3.3; the opening and closing of the carbon dioxide passage 3.2 are controlled by controlling the opening and closing of the carbon dioxide passage switch 3.2.3; the opening and closing of the mixed gas suction passage 3.4 are controlled by controlling the opening and closing of the mixed gas suction pump 3.4.1.

In an embodiment, the opening and closing of the oxygen passage switch 3.3.3, the carbon dioxide passage switch 3.2.3, and the mixed gas suction passage 3.4 are controlled by an algorithm. Opening and closing times of the gas passage switches are controlled by the algorithm according to the real-time gas concentration values in the incubator 1 so that the real-time gas concentration values in the incubator 1 are close to or equal to the preset values respectively.

In an embodiment, the opening and closing of the mixed gas suction passage 3.4 are adjusted by adjusting the opening and closing of the mixed gas suction pump 3.4.1.

In an embodiment, the on-off time of the carbon dioxide passage may be adjusted in a hierarchical manner according to the value of $C_{CO2}$. For example, the carbon dioxide passage has a shorter opening period between two measurements when $C_{CO2}$ is smaller.

In an embodiment, the on-off time of the oxygen passage switch may be adjusted in a hierarchical manner according to the value of $C_{O2}$. For example, the oxygen passage has a shorter the opening period between two measurements when $C_{O2}$ is smaller.

The value of $C_{CO2}$ and $C_{O2}$ may fall within several levels of ranges. The levels can be flexibly designed. In some embodiments, there are 10 levels, and they are level 1, level 2, level 3, level 4, level 5, level 6, level 7, level 8, level 9, and level 10.

The gas flow rates of the carbon dioxide passage or the oxygen passage are constant during ventilation, and the ventilation volume may be adjusted by controlling the on-off time of the passage switches. The longer the opening period, the greater the ventilation volume.

Further, to ensure uniform gas mixing, the gas concentration values may be measured by the gas concentration sensor segment after the oxygen passage or carbon dioxide passage is closed and the gas is fully mixed. That is, after the gas is inputted and the passages are closed, the gas is left mixing for a period of time, and then the gas concentration values are measured by the gas concentration sensor segment. In general, the shorter the ventilation time is, the shorter the time needed for mixing is. The gas refers to oxygen or carbon dioxide. The passage refers to oxygen passage or carbon dioxide passage.

Take an incubator with the dimension of 373 mm×330 mm×250 mm as an example:

In some embodiments, all possible values of $C_{CO2}$ are divided into seven levels: $C_{CO2} \geq 2\%$, $1\% \leq C_{CO2} < 2\%$, $0.8\% \leq C_{CO2} < 1\%$, $0.5\% \leq C_{CO2} < 0.8\%$, $0.3\% \leq C_{CO2} < 0.5\%$, $0.1\% < C_{CO2} < 0.3\%$, and $C_{CO2} \leq 0.1\%$. When ventilating, the gas flow rate is constant. When $C_{CO2}$ is greater than or equal to 2%, the carbon dioxide passage switch is controlled to be opened for 1.5 seconds and then closed, the gas is then left mixing for 12 seconds, and the real-time carbon dioxide gas concentration value $C_{tCO2}$ is then measured by the carbon dioxide gas concentration sensor and compared with the preset carbon dioxide gas concentration value $C_{0CO2}$. When $1\% \leq C_{CO2} < 2\%$, the carbon dioxide passage switch is controlled to be opened for 1 seconds and then closed, the gas is then left mixing for 9 seconds, and the real-time carbon dioxide gas concentration value $C_{tCO2}$ then measured by the carbon dioxide gas concentration sensor and compared with the preset carbon dioxide gas concentration value $C_{0CO2}$. When $0.8\% \leq C_{CO2} < 1\%$, the carbon dioxide passage switch is controlled to be opened for 0.8 seconds and then closed, the gas is then mixed for 3 seconds, and the real-time carbon dioxide gas concentration value $C_{tCO2}$ is then measured by the carbon dioxide gas concentration sensor and compared with the preset carbon dioxide gas concentration value $C_{0CO2}$. When $0.5\% \leq C_{CO2} < 0.8\%$, the carbon dioxide passage switch is controlled to be opened for 0.6 seconds and then closed, and the real-time carbon dioxide gas concentration value $C_{tCO2}$ is then immediately measured by the carbon dioxide gas concentration sensor and compared with the preset carbon dioxide gas concentration value $C_{0CO2}$. When $0.3\% \leq C_{CO2} < 0.5\%$, the carbon dioxide passage switch is controlled to be opened for 0.5 seconds and then closed, and the real-time carbon dioxide gas concentration value $C_{tCO2}$ is then immediately measured by the carbon dioxide gas concentration sensor and compared with the preset carbon dioxide gas concentration value $C_{0CO2}$. When $0.1\% < C_{CO2} < 0.3\%$, the carbon dioxide passage switch is controlled to be opened for 0.3 seconds and then closed, and the real-time carbon dioxide gas concentration value $C_{tCO2}$ is then immediately measured by the carbon dioxide gas concentration sensor and compared with the preset carbon dioxide gas concentration value $C_{0CO2}$. When $C_{CO2} \leq 0.1\%$, the carbon dioxide passage switch remains closed.

In some embodiments, all possible values of $C_{O2}$ are also divided into seven levels: $C_{O2} \geq 2\%$, $1\% \leq C_{O2} < 2\%$, $0.8\% \leq C_{O2} < 1\%$, $0.5\% \leq C_{O2} < 0.8\%$, $0.3\% \leq C_{O2} < 0.5\%$, $0.1\% < C_{O2} < 0.3\%$, and $C_{O2} \leq 0.1\%$. When ventilating, the gas flow rate is constant, when $C_{O2}$ is greater than or equal to 2%, the oxygen passage switch is controlled to be opened for 1.5 seconds and then closed, then the gas is left mixing for 12 seconds, and the real-time oxygen gas concentration value $C_{tO2}$ is then measured by the oxygen gas concentration sensor and compared with the preset oxygen gas concentration value $C_{0O2}$; when $1\% \leq C_{O2} < 2\%$, the oxygen passage switch is controlled to be opened for 1 seconds and then closed, then the gas is left mixing for 9 seconds, and the real-time oxygen gas concentration value $C_{tO2}$ is then measured by the oxygen gas concentration sensor and compared with the preset oxygen gas concentration value $C_{0O2}$; when $0.8\% \leq C_{O2} < 1\%$, the oxygen passage switch is controlled to be opened for 0.8 seconds and then closed, then the gas is left mixing for 3 seconds, and the real-time oxygen gas concentration value $C_{tO2}$ then measured by the oxygen gas concentration sensor and compared with the preset oxygen gas concentration value $C_{0O2}$; when $0.5\% \leq C_{O2} < 0.8\%$, the oxygen passage switch is controlled to be opened for 0.6 seconds and then closed, and the real-time oxygen gas concentration value $C_{tO2}$ is then immediately measured by the oxygen gas concentration sensor and compared with the preset oxygen gas concentration value $C_{0O2}$; when $0.3\% \leq C_{O2} < 0.5\%$, the oxygen passage switch is controlled to be opened for 0.5 seconds and then closed, and the real-time oxygen gas concentration value $C_{tO2}$ is then immediately measured by the oxygen gas concentration sensor and compared with the preset oxygen gas concentration value $C_{0O2}$; when $0.1\% < C_{O2} < 0.3\%$, the oxygen passage switch is controlled to be opened for 0.3 seconds and then closed, and the real-time oxygen gas concentration value $C_{tO2}$ is then immediately measured by the oxygen gas concentration sensor and compared with the preset oxygen gas concentration value $C_{0O2}$; when $C_{O2} \leq 0.1\%$, the oxygen passage switch remains closed.

The liquid flow assembly includes a liquid inlet passage 4.1, a circulation passage 4.2, a waste liquid passage 4.3, and a harvest passage 4.4. The liquid inlet passage 4.1 and the circulation passage 4.2 are respectively connected with the bioreactor 2. The liquid inlet passage 4.1 is configured to feed liquid into the bioreactor 2, and the circulation passage 4.2 is configured to filter metabolites produced by cells. The waste liquid passage 4.3 is in communication with the circulation passage 4.2, and discharges the metabolites. The harvest passage 4.4 is in communication with the bioreactor 2, and recovers finished cells. The flow control components of the liquid inlet passage 4.1, the circulation passage 4.2, the waste liquid passage 4.3 and the harvest passage 4.4 are controlled by the central controller 6.

The flow control component may be a flow pump or a flow control switch.

The liquid inlet passage 4.1 includes a liquid storage bag 4.1.1, a liquid inlet pipeline 4.1.2, and a liquid inlet pump 4.1.3. The liquid storage bag 4.1.1 is in communication with the liquid inlet pipeline 4.1.2. The liquid inlet pipeline 4.1.2 is driven by the liquid inlet pump 4.1.3, and the liquid inlet pipeline 4.1.2 is in communication with the bioreactor 2. The liquid inlet pump 4.1.3 is controlled by the central controller 6. The liquid in the liquid storage bag may be replaced as needed. For example, the liquid may be culture medium or normal saline. The culture medium may be a liquid culture medium.

Further, the liquid inlet pipeline 4.1.2 is provided with a cell branch pipe. Cells may be injected into the bioreactor through the branch pipe. After the cells are injected, the branch pipe is closed. For example, a branch pipe cover may be provided to close the branch pipe.

In an embodiment, the liquid inlet passage 4.1 further includes a liquid level gauge 4.1.5. The liquid level gauge 4.1.5 is disposed on the liquid inlet pipeline 4.1.2 and is connected with the central controller, to detect the liquid level change in the liquid inlet pipeline. Data representing the liquid level in the liquid inlet pipeline is sent to the central controller 6 in real time.

The circulation passage 4.2 includes a circulation pipeline 4.2.1, a circulation pump 4.2.2 and a filter 4.2.3. The circulation pipeline 4.2.1 is connected with the bioreactor 2. The filter 4.2.3 is disposed on the circulation pipeline 4.2.1 and connected with the circulation pipeline 4.2.1. The circulation pipeline 4.2.1 is driven by the circulation pump 4.2.2. The circulation pump 4.2.2 is controlled by the central controller 6.

In an embodiment, the filter 4.2.3 may be a hollow fiber column.

In an embodiment, the waste liquid passage 4.3 includes a waste liquid pump 4.3.1, a waste liquid barrel 4.3.2, and a waste liquid pipeline 4.3.3. The waste liquid pipeline 4.3.3 is connected with the circulation passage 4.2, the waste liquid barrel 4.3.2 is connected with the waste liquid pipeline 4.3.3, and the waste liquid pipeline 4.3.3 is driven by the waste liquid pump 4.3.1. The waste liquid pump 4.3.1 is controlled by the central controller 6.

In an embodiment, the harvest passage 4.4 includes a harvest pipeline 4.4.1, a harvest pump 4.4.2 and a harvest bag 4.4.3. The harvest pipeline 4.4.1 is connected with the bioreactor 2. The harvest pipeline 4.4.1 is driven by the harvest pump 4.4.2. The harvest bag 4.4.3 is in connected with the harvest pipeline 4.4.1. The harvest pump 4.4.2 is controlled by the central controller 6.

In an embodiment, the culture system is provided with a harvest bag placing tray for placing the harvest bag. An antiskid reinforcement is provided on the harvest bag placing tray.

Figure 5:
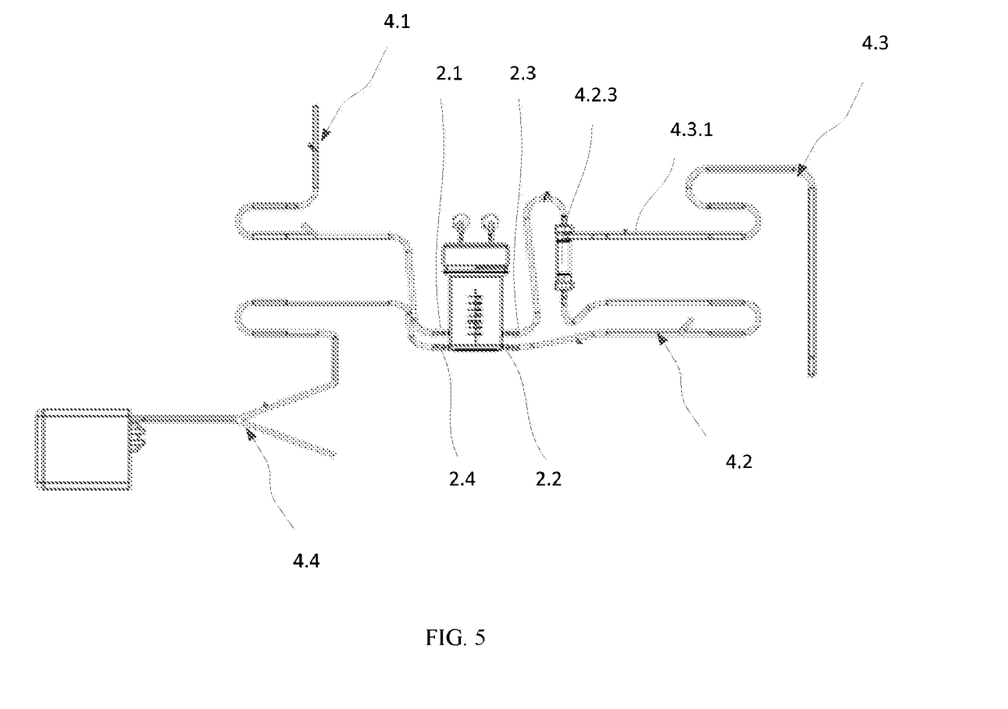
FIG. 5 is a schematic diagram showing connections between a bioreactor and a liquid flow assembly of a fully enclosed cell culture system according to some embodiments.

Further, as shown in FIG. 5, a side wall of the bioreactor 2 is provided with four ports: a liquid inlet 2.1, to connect with the liquid inlet passage 4.1; a first circulation port 2.2 and a second circulation port 2.3, to connect with the circulation passage 4.2; a harvest port 2.4, to connect with the harvest passage 4.4.

As shown in FIG. 5, during the cell culture process, when the circulation passage 4.2 is open, the mixture of cell culture medium and cells in the bioreactor are driven by the circulation pump and discharged from the first circulation port 2.2 into the filter 4.2.3 of the circulation passage 4.2. The filter 4.2.3 has a membrane with a pore size of 0.2-1 micrometers, which enables water and components of metabolic waste generated by cell culture in the medium to pass through the filter 4.2.3, while preventing the cells from passing through the filter 4.2.3. Therefore, part of the culture medium and waste liquid formed by metabolic waste is filtered, and the remaining part of the culture medium and cells re-enter the bioreactor 2 through the second circulation port 2.3.

During the cell culture process, the circulation passage may be opened or closed according to user needs.

Further, the filter 4.2.3 is provided with a waste liquid chamber for temporarily storing waste liquid. The filter 4.2.3 is provided with a first outlet and a second outlet. The first outlet is configured to re-transport the remaining part of the culture medium and cells to the bioreactor. The second outlet is configured to connect with the waste liquid chamber and the waste liquid pipeline 4.3.3 to discharge waste liquid.

The first circulation port 2.2 and the harvest port 2.4 are both disposed at the bottom of the side wall of the bioreactor, to fully suck out the cells and liquid in the bioreactor 2.

In an embodiment, the liquid flow assembly 4 includes a weighing sensor 4.5. The weighing sensor 4.5 is configured to measure the weight of the bioreactor in real time. The weighing sensor 4.5 is located at the bottom of the bioreactor, and provides detection information to the central controller 6.

The central controller includes a liquid control segment. The central controller may receive user instructions and control the on/off status of the liquid inlet passage, the circulation passage, the waste liquid passage, and the harvest passage according to the user instructions.

During the cell culture process, a user may give instructions to set the liquid feeding volume and waste liquid discharge volume according to needs. In an embodiment, the central controller 6 may calculate liquid weight according to volume and density, and then control the liquid feeding volume and waste liquid discharge volume using a weighing sensor. When no liquid is fed into the culture at the beginning of the culture the bioreactor is tared, and then during the culture process the weight of the bioreactor read by a user is equal to the weight of the contents in the bioreactor.

In an embodiment, the central controller 6 includes a weight comparison unit and a liquid inlet passage on-off control unit. During the perfusion process, the weight comparison unit compares a real-time bioreactor weight $M_t$ measured by the weighing sensor and a first preset bioreactor weight $M_{in0}$ given by the user; a first weight difference $M_{in}$ is then obtained according to the formula (III):

$$M_{in}=M_{in0}-M_t \quad (III)$$

The liquid inlet passage on-off control unit is configured to control the on/off of the liquid inlet passage according to the value of $M_{in}$.

More specifically, when $M_{in}$ is greater than 0, the liquid inlet passage is turned on; when $M_{in}$ is equal to or less than 0, the liquid inlet passage is turned off.

The central controller further includes a waste liquid passage on-off control unit. When the liquid is discharged, the weight comparison unit compares the real-time bioreactor weight $M_t$ measured by the weighing sensor with the a second preset bioreactor weight $M_{out0}$ given by the user; a second weight difference $M_{out}$ is obtained according to the formula (IV):

$$M_{out}=M_t-M_{out0} \quad (IV)$$

The waste liquid passage on-off control unit controls the on/off of the waste liquid passage according to the value of $M_{out}$. More specifically, when $M_{out}$ is greater than 0, the waste liquid passage is turned on; when $M_{out}$ is equal to or less than 0, the waste liquid passage is turned off.

The temperature adjustment assembly 5 includes a heating device 5.1 and a temperature sensor 5.2. The heating device 5.1 and the temperature sensor 5.2 are disposed in the incubator 1 and are connected with the central controller 6 respectively. The heating device 5.1 is configured to heat the inner cavity of the incubator. The temperature sensor 5.2 is configured to measure the real-time temperature in the incubator and provide detection information to the central controller 6. The heating device 5.1 is controlled by the central controller 6. The temperature adjustment assembly may keep the bioreactor located in the incubator in a thermostatic environment, and ensures that temperature of the gas entering the bioreactor is constant.

In an embodiment, a temperature value $T_0$ is preset, and the temperature value may be suitable for cell culture; the temperature sensor provides the central controller with a real-time temperature value $T_t$ in the incubator, and the central controller 6 compares $T_t$ with $T_0$; when $T_t$ is less than $T_0$, the central controller instructs the heating device to start; when $T_t$ is greater than or equal to $T_0$, the central controller instructs the heating device to stop running.

The heating device 5.1 may be a heating plate, which is attached to an inner wall of the incubator.

The heating plate and temperature sensor are all commercially available products.

Figure 6:
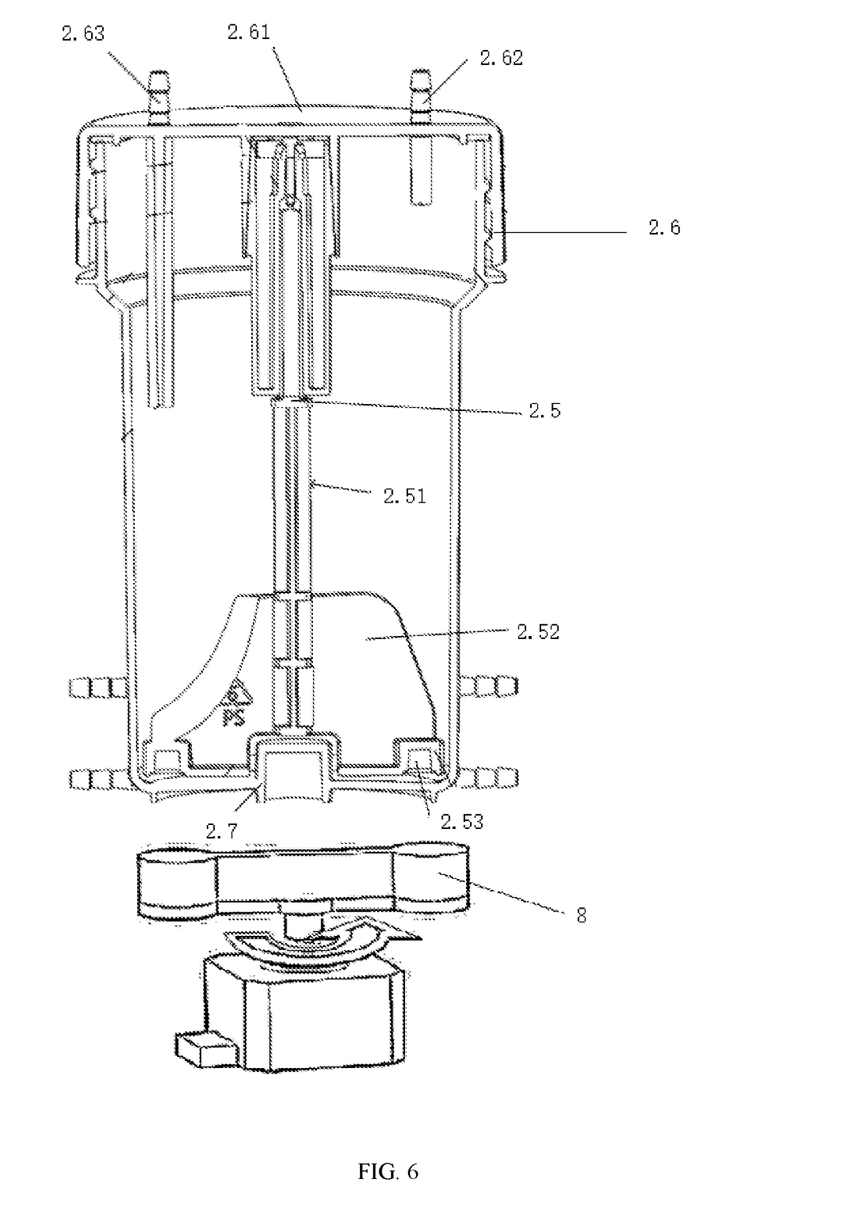
FIG. 6 is a cross-sectional view of a bioreactor of a fully enclosed cell culture system according to some embodiments.
Figure 7:
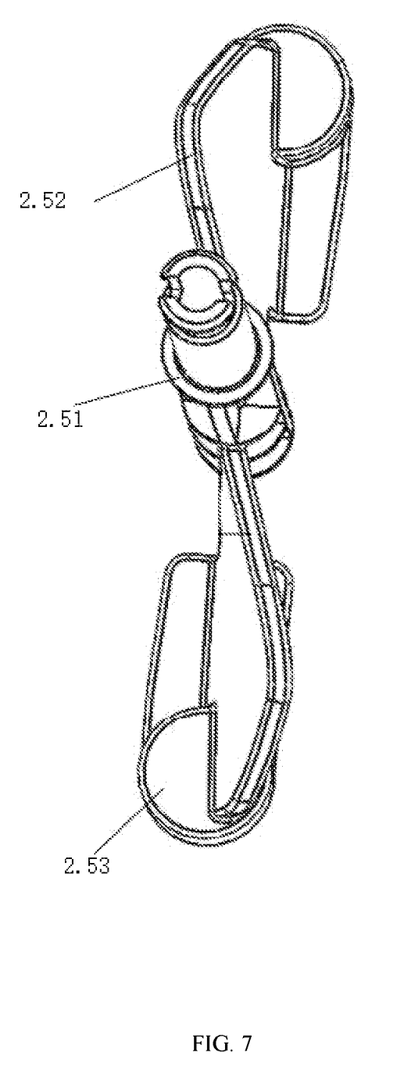
FIG. 7 is a top perspective view of a bioreactor stirrer of a fully enclosed cell culture system according to some embodiments.

As shown in FIGS. 6 and 7, the stirrer 2.5 includes: a center shaft 2.51, and at least two blades 2.52, which are rotationally symmetric about the axis of the center shaft and connected to the center shaft. Each of the blades includes a blade body, the blade body is helically extended, the axial length of the blade body accounts for 20% to 35% of the length of the center shaft, the rotation angle of the blade body is 15° to 50°, the maximum radial length of the blade body is 20 mm to 54 mm, and the radial length of the blade body gradually decreases from bottom to top. The use of blades of the above-mentioned shape may reduce shearing forces on the T cells and help the T cells and the culture system be stirred uniformly.

Further, from bottom to top, the radial length of the blade body decreases linearly with the axial height.

The helical shape of the blade body is formed on the basis of a regular helical surface, and is the part of the regular helical surface that remains within a conical surface after the conical surface excises the regular helical surface. The half cone angle of the conical surface is within the range of 20-45 degrees. A blade of a helical shape may reduce the space between the blade and the side wall of the tank where radial vortexes form while achieving the technical effect of rolling cells and the culture medium up and down in the axial direction, so as to reduce the shearing forces generated during the stirring process, thereby protecting T cells and improving the yield of T cells.

The bottom surface of the bioreactor includes an inner recess 2.7 at the center of the bottom surface of the bioreactor, for fixing the bioreactor.

The culture system includes a stirring driver 8 for driving the stirrer. The stirring driver is controlled by the central controller 6.

In an embodiment, the blade further includes an enclosed accommodating chamber 2.53 at a maximum radial length of the blade body for accommodating a magnet that drives the stirrer to rotate. In this case, the stirring driver 8 is a magnetic driver. The magnetic driver generates a magnetic effect on the magnet to drive the stirrer to rotate. The stirrer is driven in a non-contact way using the principle of magnetic stirring. Compared with the method of directly driving the rotating shaft of the stirring driver by a motor, the method of magnetic stirring ensures that the cell culture environment in the bioreactor is clean and convenient to maintain. The reason is that when using a motor to directly drive the rotating shaft of the stirring driver, the motor usually needs to be placed outside the bioreactor, which means that the rotating shaft of the stirrer must extend out of the bioreactor. In this case, it is necessary to ensure a strict seal between the rotating shaft of the stirrer and the bioreactor for a long time in the culture environment, which increases the complexity of the system and makes it difficult to maintain. Moreover, wear of the sealing elements may also cause pollution to the culture system.

The blade of the stirrer of the present disclosure is designed with a helical surface and specific axial and radial dimensions. As a result, in the culture system, the cells and culture medium are stirred axially in the tank body. The radial shear forces are reduced, which protects the cells and improves the cell yield.

The bioreactor 2 further includes an incubation cover 2.6. The incubation cover 2.6 is in a closed state during the culture process.

Further, as shown in FIG. 6, the incubation cover 2.6 of the bioreactor 2 includes a cover body 2.61, a gas intake part 2.63, and a gas exhaust part 2.62 provided on the cover body 2.61. The gas intake part 2.63 is configured to convey gas to the inner space of the bioreactor, and the gas exhaust part 2.62 is configured to exhaust gas from the inner space of the bioreactor. The length of the gas intake part 2.63 in the direction perpendicular to the bottom surface of the cover body is greater than that of the gas exhaust part 2.62. During cell culture, the gas intake part is configured to convey gas into the bioreactor. During cell culture, the gas intake part conveys gas by using a non-contact conveying method. That is, the structure of the gas intake part has no contact with the culture medium. One advantage of one or more aspects of such a design is that compared with the traditional technology (in which a gas intake pipe is extended into the culture medium, resulting in bubbles in the culture system and damage to T cells), a non-contact convey is better at preventing the formation of bubbles and improve the T cell yield. In addition, the length of the gas intake part in the direction perpendicular to the bottom surface of the cover body is greater than that of the gas exhaust part. One advantage of one or more aspects of such a design is that the oxygen concentration and carbon dioxide concentration in the culture system may be adjusted more quickly compared with the design where the length of the gas intake part is equal to or shorter than that of the gas exhaust part. The gas composition of the intake gas is adjusted according to the different stages of the culture. In the initial stage, the proportion of carbon dioxide in the intake gas is appropriately increased; as the culture progresses, cell respiration produces a certain amount of carbon dioxide, and therefore, the proportion of carbon dioxide in the intake gas may be reduced accordingly.

In an embodiment, an ultraviolet sterilizing lamp is provided in the incubator 4 for sterilizing the incubator.

In an embodiment, the culture system includes an alarm segment, and the alarm segment is driven by the central controller 6. Alarm thresholds of the liquid flow assembly, the gas flow assembly, and the temperature adjustment assembly are preset. The central controller controls the alarm segment to issue an alarm when receiving detection information showing that the liquid flow assembly, the gas flow assembly and the temperature adjustment assembly exceed the alarm thresholds.

The central controller may be a single-chip microcomputer, which may be an 8-bit minimum system. The central controller may be of different brands and models. The central controller may be a controller or processor with higher digits. The central controller may be configured to install a related control program. After installing the related control program, the central controller may receive signals from the liquid flow assembly, gas flow assembly and the temperature adjustment assembly, and user instructions, and adjust the parameters of the components in the assemblies as needed to make the system run smoothly.

Further, the bioreactor is made of one or more materials that are not air permeable.

The bioreactor and/or accessories of the bioreactor may exchange gas or liquid with the outside only through the various passages.

The incubator further includes an incubator door; the incubator door isolates the incubator from the external environment, so that a relatively independent environment is formed inside the incubator.

A fully enclosed cell culture structure means that the entire culture environment (including tanks, filters, pipelines, etc.) is in a relatively closed state during the entire process of cell culture from activation, infection and amplification to finished product harvesting, that the entire culture environment is only connected with the outside through sterile gas passages or liquid passages, and that the incubator is relatively independent from the external environment, so that the environment in the incubator is within a controllable range.

The fully enclosed cell culture system of the present disclosure may be used for fully enclosed cell culture.

The present disclosure provides a method for fully enclosed cell culture using the aforementioned fully enclosed cell culture system, including the following operations:

1) perfusion: presetting a liquid volume, and injecting culture medium into a bioreactor, the volume of the injected culture medium equals the preset liquid volume;
2) establishing a culture environment: presetting concentration values of oxygen and carbon dioxide, injecting oxygen and carbon dioxide into the incubator, monitoring gas concentration values of oxygen and carbon dioxide in the incubator in real time, and comparing the gas concentration values with the preset concentration values respectively; when the oxygen and carbon dioxide's concentration values in the incubator reach a threshold, injecting the gas in the incubator into the bioreactor; setting a temperature for the incubator and preheating the incubator;

3) continuous culturing: injecting cells, injecting factors, starting a stirrer, injecting the culture medium into the bioreactor, filtering metabolites, and discharging waste liquid;

4) replacing and concentrating: after the cell culture is completed, replacing the culture medium with saline solution; performing concentration after the replacement is completed; continuously discharging the waste liquid to reduce the amount of liquid in the bioreactor;

5) harvesting finished products: stopping the stirrer and harvesting finished cells in the bioreactor.

In operation 1), the culture medium is injected into the bioreactor through a liquid inlet passage. Specifically, the volume of culture medium to be injected into the bioreactor is preset, a first preset bioreactor weight $M_{in0}$ is calculated according to the preset volume, a liquid inlet pump is started, culture medium in a liquid storage bag is injected into the bioreactor through a liquid inlet pipeline, and the amount of extra culture medium required to be injected into the bioreactor is determined by using a weighing sensor to measure a real-time bioreactor weight $M_t$ measured by a weighing sensor, $M_t$ is compared with the first preset bioreactor weight $M_{in0}$, and a first weight difference $M_{in}$ is obtained according to the formula (III):

$$M_{in}=M_{in0}-M_t \quad (III)$$

The on/off of the liquid inlet passage is controlled according to the value of $M_{in}$. More specifically, when $M_{in}$ is greater than 0, the liquid inlet passage is turned on; when $M_{in}$ is equal to or less than 0, the liquid inlet passage is turned off.

In operation 2), oxygen and carbon dioxide are injected into the incubator through the oxygen passage and the carbon dioxide passage respectively, and the gas in the incubator is injected into the bioreactor through the mixed gas suction passage. The gas concentration value of carbon dioxide in the incubator is measured by a carbon dioxide gas concentration sensor, and the gas concentration value of oxygen in the incubator is measured by an oxygen gas concentration sensor. A real-time oxygen gas concentration value $C_{tO2}$ and a real-time carbon dioxide gas concentration value $C_{tCO2}$ are compared with a preset oxygen gas concentration value $C_{0O2}$ and a preset carbon dioxide concentration value $C_{0CO2}$, respectively; $C_{O2}$ is the difference between $C_{0CO2}$ and $C_{tO2}$; $C_{CO2}$ is the difference between $C_{0CO2}$ and $C_{tCO2}$ as given by formulas (I) and (II):

$$C_{O2}=C_{0O2}-C_{tO2} \quad (I)$$

$$C_{CO2}=C_{0CO2}-C_{tCO2} \quad (II)$$

In operation 2), the on-off time of the oxygen passage is then adjusted according to the value of $C_{O2}$; the on-off time of the carbon dioxide passage is adjusted according to the value of $C_{CO2}$; when both $C_{O2}$ and $C_{CO2}$ fall within set threshold range, the mixed gas suction passage is opened, and the gas in the incubator is sucked into the bioreactor; when either $C_{O2}$ or $C_{CO2}$ does not fall within its corresponding preset range, the mixed gas suction passage 3.4 is closed.

In an embodiment, the on-off time of the oxygen passage may be adjusted in a hierarchical manner according to the value of $C_{CO2}$. In an embodiment, the on-off time of the carbon dioxide passage switch may be adjusted in a hierarchical manner according to the value of $C_{CO2}$.

In an embodiment, the gas flow may be agitated with a fan, to speed up the mixing and make the gas in the incubator 1 more evenly mixed.

In operation 3), the cells are injected through a liquid inlet passage, and metabolites are filtered through a circulation passage. The circulation passage is provided with a filter and a circulation pump. After starting the stirrer the culture process starts, and the circulation passage may be opened according to the needs of the culture. When the circulation passage is in the open state, the mixture of cell culture medium and cells in the bioreactor is driven by the circulation pump and discharged from a first circulation port of the bioreactor into a filter of the circulation passage. The filter has a membrane with a pore size of 0.2-1 micrometers, which enables water and components of metabolic waste generated by cell culture in the culture medium to pass through the filter, while preventing the cells from passing through the filter. Therefore, part of the culture medium and waste liquid formed by metabolic waste is filtered and temporarily stored in a waste liquid chamber on the filter; remaining part of the culture medium and cells re-enter the bioreactor through a second circulation port of the bioreactor. The filter is provided with a first outlet and a second outlet. The remaining part of the culture medium and cells are re-transported into the bioreactor through the first outlet. When the waste liquid is to be discharged, the waste liquid passage is opened. A waste liquid discharge volume is preset, and a second preset bioreactor weight $M_{out0}$ is then preset according to the waste liquid discharge volume. The waste liquid is discharged into a waste liquid pipeline through the second outlet, and then into a waste liquid barrel. The real-time bioreactor weight $M_t$ measured by the weighing sensor is compared with the a preset bioreactor weight $M_{out0}$; a second weight difference $M_{out}$ is obtained according to the formula (IV):

$$M_{out}=M_t-M_{out0} \quad (IV)$$

Still in operation 3), the on/off of the waste liquid passage is then controlled according to $M_{out}$. More specifically, when $M_{out}$ is greater than 0, the waste liquid passage is turned on; when $M_{out}$ is equal to or less than 0, the waste liquid passage is turned off.

When more culture medium is needed, a liquid feeding volume is preset, a preset bioreactor weight $M_{in0}$ is obtained according to the liquid feeding volume, a liquid inlet pump is started, culture medium in the liquid storage bag is injected into the bioreactor through the liquid inlet pipeline, and the amount of culture medium needed to be injected into the bioreactor is determined by using a weighing sensor to measure the real time bioreactor weight; the real-time bioreactor weight $M_t$ measured by the weighing sensor is compared with the preset bioreactor weight $M_{in0}$; a weight difference $M_{in}$ is obtained according to the formula (III):

$$M_{in}=M_{in0}-M_t \quad (III)$$

The on/off of the liquid inlet passage is controlled according to $M_{in}$. Further, when $M_{in}$ is greater than 0, the liquid inlet passage is turned on; when $M_{in}$ is equal to or less than 0, the liquid inlet passage is turned off.

Further, during the culture process, the circulation passage may be opened or closed according to user needs.

In operation 4), after the cell culture is completed, the culture medium is replaced with normal saline. More specifically, after discharging a certain amount of waste liquid, an equal amount of normal saline is added; the above operation is repeated until the culture medium is completely replaced. In some embodiments, if the initial volume of liquid in the bioreactor is 400 ml, firstly 200 ml of waste liquid is discharged, then 200 ml of normal saline is added, and as a result, the concentration of the culture medium is reduced to 50% of the original; after the operation is repeated for 10 times, the concentration of the culture medium is reduced to the $(½)^{10}$ of the original, and the replacement may be considered complete. Then the waste liquid is continuously discharged, so that the volume of liquid in the bioreactor is further reduced.

During the concentration process, the volume of liquid in the bioreactor is controlled. The control method is: a target bioreactor weight is set as M; the real-time bioreactor weight $M_t$ measured by the weighing sensor is compared with the target bioreactor weight M; a third weight difference $M_1$ is obtained according to the formula (V):

$$M_1 = M_t - M \quad (V)$$

The on/off of the waste liquid passage is controlled according to $M_1$. Further, when $M_1$ is greater than 0, the waste liquid passage is turned on; when $M_1$ is equal to or less than 0, the waste liquid passage is turned off In operation 5), finished cells are harvested using a cell harvest passage. Specifically, driven by a harvest pump, the cell-containing mixture in the bioreactor passes through a harvest port and enters a harvest bag through a harvest pipeline.

Further, in operation 5), the circulation pump may be operated in reverse, so that the finished cells in the circulation passage are harvested.

In an embodiment, operation 2) includes preprocessing the filter;

In an embodiment, the liquid inlet passage further includes a liquid level gauge. Changes of the liquid level in the liquid inlet pipeline are monitored by using the liquid level gauge.

In an embodiment, the culture system includes an alarm segment. Alarm thresholds of the liquid level, oxygen gas concentration, carbon dioxide gas concentration, bioreactor weight and temperature in the system are pre-set. Each of the alarm thresholds includes an alarm upper threshold and an alarm lower threshold. When any of the liquid level, oxygen gas concentration, carbon dioxide gas concentration, bioreactor weight and temperature is higher than its corresponding alarm upper threshold or lower than its corresponding alarm lower threshold, an alarm is generated.

In an embodiment, an ultraviolet sterilizing lamp is provided in the incubator for sterilizing the incubator.

The opening and closing of the liquid inlet passage, the circulation passage and the waste liquid passage in the liquid flow assembly, the volume of liquid feeding, and the waste liquid discharge volume may be controlled on-site by users according to the culture condition during the culture process, and corresponding operations may be immediately performed. The settings may also be completed in advance, and the operations may be implemented by a timed starting of the system.

In summary, the system of the present disclosure realizes a thermostatic incubation environment. Cells are incubated by perfusion, and therefore waste liquid may be discharged during the incubation process to prevent the accumulation of harmful metabolites, which is beneficial for achieving a high cell culture density; further, subsequent processing steps may be reduced, and the finished cells may be harvested without centrifugation and other operations; the operations may be simplified, the culture efficiency is improved, the industrialization is facilitated, and a fully enclosed integrated process from cell activation, infection and amplification to finished product harvesting is achieved. By axially stirring the cells and incubation liquid in a tank body, radial shear force are reduced, which protects the cells and improves the cell yield. In the system of the present disclosure, gases are separately introduced, and the content of each gas component is stabilized in the incubation process, which ensures that the cell incubation is not directly affected by changes of outside gases in the cell incubation process, and that the content of each gas component is unchanged, while reducing manual operations, reducing the costs, reducing the risk of operating errors in the incubation process, and improving culture efficiency. Therefore, the present disclosure effectively overcomes various shortcomings in traditional technology and has high industrial utilization value.

The above-mentioned embodiments are merely illustrative of the present disclosure and are not a limitation of the present disclosure. Modifications or variations of the above-described embodiments may be made by those skilled in the art without departing from the spirit and scope of the disclosure. Therefore, all equivalent modifications or changes made by those skilled in the art without departing from the spirit and technical concept disclosed by the present disclosure shall be still covered by the claims of the present disclosure.

The invention claimed is:

1. A fully enclosed cell culture system, comprising at least the following:
   an incubator (1);
   an bioreactor (2) to perform cell culture, disposed in the incubator (1), wherein the bioreactor (2) includes a stirrer (2.5), and the stirrer (2.5) is disposed in the bioreactor;
   a gas flow assembly (3), connected with the incubator (1), wherein the gas flow assembly (3) adjusts concentrations of oxygen and carbon dioxide in the incubator (1);
   a liquid flow assembly (4), connected with the bioreactor (2), wherein the liquid flow assembly (4) adjusts a liquid flow in the bioreactor (2), filters metabolites produced during cell culture, and recovers finished cells;
   a temperature adjustment assembly (5), wherein the temperature adjustment assembly (5) adjusts temperature in the incubator (1);
   a central controller (6), connected to and controlling the gas flow assembly (3), the liquid flow assembly (4), and the temperature adjustment assembly (5);
   wherein the liquid flow assembly (4) comprises:
   a liquid inlet passage (4.1), connected with the bioreactor (2); wherein the liquid inlet passage (4.1) feeds liquid into the bioreactor (2);
   a circulation passage (4.2), connected with the bioreactor (2); wherein the circulation passage (4.2) has a filter 4.2.3 with a membrane having a pore size of 0.2-1 micrometers, which enables waste water to pass while preventing cells from passing through, therefore, cells in the waste water re-enter the bioreactor (2);
   a waste liquid passage (4.3), wherein the waste liquid passage (4.3) is connected with the circulation passage (4.2) to discharge the metabolites; and
   a harvest passage (4.4), wherein the harvest passage (4.4) is connected with the bioreactor (2) to recover finished cells;
   wherein the gas flow assembly (3) comprises:
   an air passage (3.1), a carbon dioxide passage (3.2) and an oxygen passage (3.3), which are separated and respectively connected with the incubator (1) to deliver gas into the incubator (1) to form a gas mixture;

a mixed gas suction passage (3.4), connected with the incubator (1) and the bioreactor (2), wherein the mixed gas suction passage (3.4) delivers the gas mixture in the incubator (1) into the bioreactor (2);

an exhaust gas discharge passage (3.5), connected with the bioreactor (2), wherein the exhaust gas discharge passage (3.5) discharges exhaust gas generated during a cell culture process;

a gas concentration sensor segment (3.6), including an oxygen gas concentration sensor (3.6.1) and a carbon dioxide gas concentration sensor (3.6.2), wherein the oxygen gas concentration sensor (3.6.1) measures a real-time oxygen gas concentration value, and the carbon dioxide gas concentration sensor (3.6.2) measures a real-time carbon dioxide gas concentration value in the incubator (1), wherein the gas concentration sensor segment (3.6) provides detection information to the central controller (6);

wherein the central controller (6) comprises:

a gas concentration comparison unit, wherein the gas concentration comparison unit compares a real-time oxygen gas concentration value $C_{tO2}$ measured by the gas concentration sensor segment with a preset oxygen gas concentration value $C_{0O2}$, wherein the gas concentration comparison unit compares a real-time carbon dioxide gas concentration value $C_{tCO2}$ measured by the gas concentration sensor segment (3.6) with a preset carbon dioxide gas concentration value $C_{0CO2}$, wherein $C_{O2}$ is the difference between $C_{0O2}$ and $C_{tO2}$ and $C_{CO2}$ is the difference between $C_{0CO2}$ and $C_{tCO2}$, as given by formulas (I) and (II):

$$C_{O2} = C_{0O2} - C_{tO2} \quad \text{(I)}$$

$$C_{CO2} = C_{0CO2} - C_{tCO2} \quad \text{(II); and}$$

a gas concentration switch control unit, controlling the opening and closing of the carbon dioxide passage (3.2), the oxygen passage (3.3), and the mixed gas suction passage (3.4), wherein an on-off time of the oxygen passage (3.3) is adjusted according to the value of $C_{O2}$, and an on-off time of the carbon dioxide passage (3.2) is adjusted according to the value of $C_{CO2}$, wherein the mixed gas suction passage (3.4) is opened, and gas in the incubator (1) is sucked into the bioreactor (2), when both $C_{O2}$ and $C_{CO2}$ fall within a preset range;

when the mixed gas suction passage (3.4) is closed when either $C_{O2}$ or $C_{CO2}$ does not fall within its corresponding preset range.

2. The fully enclosed cell culture system according to claim 1, wherein the gas flow assembly has one, two, or three of the following three features:

1) the carbon dioxide passage (3.2) includes a carbon dioxide storage device (3.2.1), a carbon dioxide pressure relief valve (3.2.2), a carbon dioxide passage switch (3.2.3), and a carbon dioxide pipeline (3.2.4); the carbon dioxide storage device (3.2.1) is connected with the carbon dioxide pipeline (3.2.4), the carbon dioxide pipeline (3.2.4) is driven by the carbon dioxide pressure relief valve (3.2.2), and the carbon dioxide pipeline (3.2.4) is in communication with the incubator (1); the carbon dioxide passage switch (3.2.3) is provided on the carbon dioxide passage (3.2), and the carbon dioxide passage switch (3.2.3) is controlled by the central controller (6);

2) the oxygen passage (3.3) includes an oxygen storage device (3.3.1), an oxygen pressure relief valve (3.3.2), an oxygen passage switch (3.3.3), and an oxygen pipeline (3.3.4); the oxygen storage device (3.3.1) is connected with the oxygen pipeline (3.3.4), the oxygen pipeline (3.3.4) is driven by the oxygen pressure relief valve (3.3.2), and the oxygen pipeline (3.3.4) is in communication with the incubator (1); the oxygen passage switch (3.3.3) is provided on the oxygen passage (3.3), and the oxygen passage switch (3.3.3) is controlled by the central controller (6);

3) The mixed gas suction passage (3.4) includes a mixed gas suction pump (3.4.1) and a mixed gas suction pipeline (3.4.2); the mixed gas suction pipeline (3.4.2) is driven by the mixed gas suction pump (3.4.1), and the mixed gas suction pipeline (3.4.2) injects the gas mixture from the incubator (1) into the bioreactor (2); the mixed gas suction pump (3.4.1) is controlled by the central controller (6).

3. The fully enclosed cell culture system of claim 1, wherein the fully enclosed cell culture system has one or more of the following four features:

1) The incubator (1) includes a gas discharge passage (3.7), which discharges gas in the incubator (1) and keeps air pressure in the incubator (1) stable;

2) the carbon dioxide passage (3.2) includes a carbon dioxide passage incubator inlet (3.2.5) on the incubator (1), and the oxygen passage (3.3) includes an oxygen passage incubator inlet (3.3.5) on the incubator (1); the carbon dioxide passage incubator inlet (3.2.5) and the oxygen passage incubator inlet (3.3.5) are both disposed in an upper part of the incubator (1);

3) The mixed gas suction passage (3.4) includes a mixed gas passage incubator outlet (3.4.3) on the incubator (1); the mixed gas passage incubator outlet (3.4.3), the oxygen gas concentration sensor (3.6.1) and the carbon dioxide gas concentration sensor (3.6.2) are disposed in a lower part of the incubator (1);

4) The incubator (1) includes a fan (3.8) for agitating a gas flow, speeding up gas mixing, making gas in the incubator (1) more evenly mixed, and accelerating heat exchange inside the incubator (1).

4. The fully enclosed cell culture system of claim 1, wherein the central controller (6) controls flow control components of the liquid inlet passage (4.1), the circulation passage (4.2), the waste liquid passage (4.3) and the harvest passage (4.4).

5. The fully enclosed cell culture system according to claim 4, wherein the liquid flow assembly has one or more of the following four features:

1) The liquid inlet passage (4.1) includes a liquid storage bag (4.1.1), a liquid inlet pipeline (4.1.2) and a liquid inlet pump (4.1.3); the liquid storage bag (4.1.1) is connected with the liquid inlet pipeline (4.1.2); the liquid inlet pipeline (4.1.2) is driven by the liquid inlet pump (4.1.3), and the liquid inlet pipeline (4.1.2) is connected with the bioreactor (2); the liquid inlet pump (4.1.3) is controlled by the central controller (6);

2) the circulation passage (4.2) includes a circulation pipeline (4.2.1), a circulation pump (4.2.2) and a filter (4.2.3); the circulation pipeline (4.2.1) is connected with the bioreactor (2); the filter (4.2.3) is disposed on the circulation pipeline (4.2.1) and communicates with the circulation pipeline (4.2.1); the circulation pipeline (4.2.1) is driven by the circulation pump (4.2.2); the circulation pump (4.2.2) is controlled by the central controller (6);

3) The waste liquid passage (4.3) includes a waste liquid pump (4.3.1), a waste liquid barrel (4.3.2), and a waste liquid pipeline (4.3.3); the waste liquid pipeline (4.3.3) is connected with the circulation passage (4.2), the waste liquid barrel (4.3.2) is connected with the waste liquid pipeline (4.3.3), and the waste liquid pipeline (4.3.3) is driven by the waste liquid pump (4.3.1); the waste liquid pump (4.3.1) is controlled by the central controller (6);

4) The harvest passage (4.4) includes a harvest pipeline (4.4.1), a harvest pump (4.4.2) and a harvest bag (4.4.3); the harvest pipeline (4.4.1) is connected with the bioreactor (2); the harvest pipeline (4.4.1) is driven by the harvest pump (4.4.2); the harvest bag (4.4.3) is connected with the harvest pipeline (4.4.1); the harvest pump (4.4.2) is controlled by the central controller (6).

6. The fully enclosed cell culture system of claim 1, wherein the fully enclosed cell culture system has one or more of the following features:

1) The liquid flow assembly (4) includes a weighing sensor (4.5), and the weighing sensor (4.5) measures a weight of the bioreactor (2) in real time; the weighing sensor (4.5) is disposed at a bottom of the bioreactor (2), and provides detection information to the central controller (6);

2) the temperature adjustment assembly (5) includes a heating device (5.1) and a temperature sensor (5.2); the heating device (5.1) and the temperature sensor (5.2) are disposed in the incubator (1) and are connected with the central controller (6) respectively; the heating device (5.1) heats an inner cavity of the incubator (1); the temperature sensor (5.2) measures a real-time temperature value in the incubator (1) and provides detection information to the central controller (6); the heating device (5.1) is controlled by the central controller (6).

7. The fully enclosed cell culture system according to claim 1, wherein the stirrer (2.5) comprises:

a center shaft (2.51); and at least two blades (2.52), wherein the blades (2.52) are rotationally symmetric about an axis of the center shaft (2.51) and connected to the center shaft (2.51), wherein each of the blades (2.52) includes a blade body, the blade body is helically extended, an axial length of the blade body accounts for 20% to 35% of a length of the center shaft (2.51), a rotation angle of the blade body ranges from 15° to 50°, a maximum radial length of the blade body ranges from 20 mm to 54 mm, and a radial length of the blade body gradually decreases from bottom to top.

\* \* \* \* \*